United States Patent [19]

Fukushige et al.

[11] Patent Number: 5,340,461
[45] Date of Patent: Aug. 23, 1994

[54] ELECTROPHORETIC MEDIUM FOR ELECTROPHORETIC SEPARATION, GEL HOLDER FOR HOLDING THE SAME MEDIUM, SLAB TYPE ELECTROPHORETIC APPARATUS USING THE SAME MEDIUM AND GEL HOLDER, AND ELECTROPHORETIC GEL CUTTER

[75] Inventors: Tomoaki Fukushige; Hiroko Toda; Hirofumi Akano; Emiko Ito; Tomohiko Fukuta; Masahiro Fujimori; Yoshiya Kawamura, all of Aichi, Japan

[73] Assignee: Nakano Vinegar Co., Ltd., Aichi, Japan

[21] Appl. No.: 12,194

[22] Filed: Feb. 2, 1993

[30] Foreign Application Priority Data

| Feb. 3, 1992 | [JP] | Japan | 4-062781 |
| Feb. 10, 1992 | [JP] | Japan | 4-069919 |
| Nov. 30, 1992 | [JP] | Japan | 4-340967 |
| Nov. 30, 1992 | [JP] | Japan | 4-340968 |

[51] Int. Cl.$^5$ .................................................. C25B 9/00
[52] U.S. Cl. ............................ 204/299 R; 204/182.8
[58] Field of Search ...................... 204/299 R, 182.8

[56] References Cited

U.S. PATENT DOCUMENTS

| 3,499,360 | 3/1970 | Davis | 204/299 R |
| 4,680,102 | 7/1987 | Ishiwatari | 204/299 R |
| 4,891,119 | 1/1990 | Ogawa | 204/182.8 |

FOREIGN PATENT DOCUMENTS

| 0134622 | 3/1985 | European Pat. Off. |
| 0137753 | 4/1985 | European Pat. Off. |
| 59-126236 | 7/1984 | Japan |
| 4-143651 | 5/1992 | Japan |

OTHER PUBLICATIONS 121119g, vol. 74, 1971. "Longitudinal Slicing of Polyacrylamide slab gels: simple technique." *Chemical Abstracts*.

Barry Ziola et al "Recovery of SDS-Proteins from Polyacrylamide Gels by Electrophoresis into Hydroxylapatite" Analytical Biochemistry 72, 1976, pp. 366-371.

Toshihisa Ohshima et al "Simple Method for Reparative Slab Gel Electrophoresis–application for the Purification of Dehydrogenase" Biochem., 60, 5., 1988, pp. 374-377.

Marion Bradford "A Rapid and Sensitive Method for the Quantitation of Microgram Quantities of Protein Utilizing the Principle of Protein-Dye Binding" Analy. Bioch. 72, 1976, pp. 248-254.

*Primary Examiner*—John Niebling
*Assistant Examiner*—Cybille Delacroix-Muirheid
*Attorney, Agent, or Firm*—Lowe, Price, LeBlanc & Becker

[57] ABSTRACT

An electrophoretic medium best suited as a separation medium is composed of a gel solution and contains a water-soluble polymer and permits great improvement of the enzymic protein recovery character. A gel holder is provided with stopper members and thus can hold even a soft or slippery while maintaining a fixed shape thereof, thus permitting reliable separation and purification of an intended substance without possibility of denaturing of the substance. A slab type electrophoretic apparatus permits automatic detection of the electrophoretic state of a sample and automatic completion of the electrophoresis under optimum conditions without setting measurement condition, permits continuous measurement of the buffer solution temperature, which is important for obtaining an electrophoretic condition for maintaining the enzymic function, and permits separation and purification of a large quantity of an enzyme or like physiologically active substance in a very simple operation. An electrophoretic gel cutter cuts even large size electrophoretic gels vary accurately and safely to desired sizes and particularly cuts a soft and readily deformable electrophoretic gel of polyacrylamide or the like in a pressurized state, thus permitting accurate and safe cutting of the polyacrylamide gel, which has been very difficult to cut, without causing damage to the gel.

22 Claims, 8 Drawing Sheets

F I G. 1
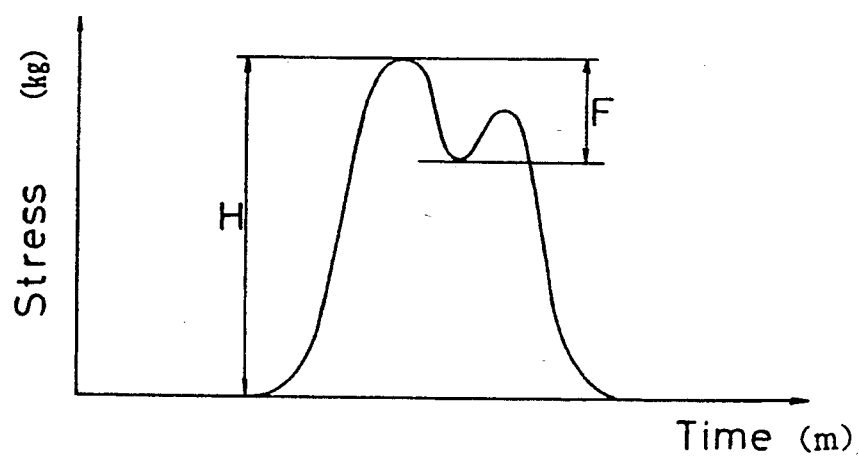

- ● ACRYLAMIDE GEL HARDNESS
- ▲ N-METHYLOLACRYLAMIDE HARDNESS
- ○ ACRYLAMIDE GEL BRITTLENESS
- △ N-METHYLOLACRYLAMIDE BRITTLENESS

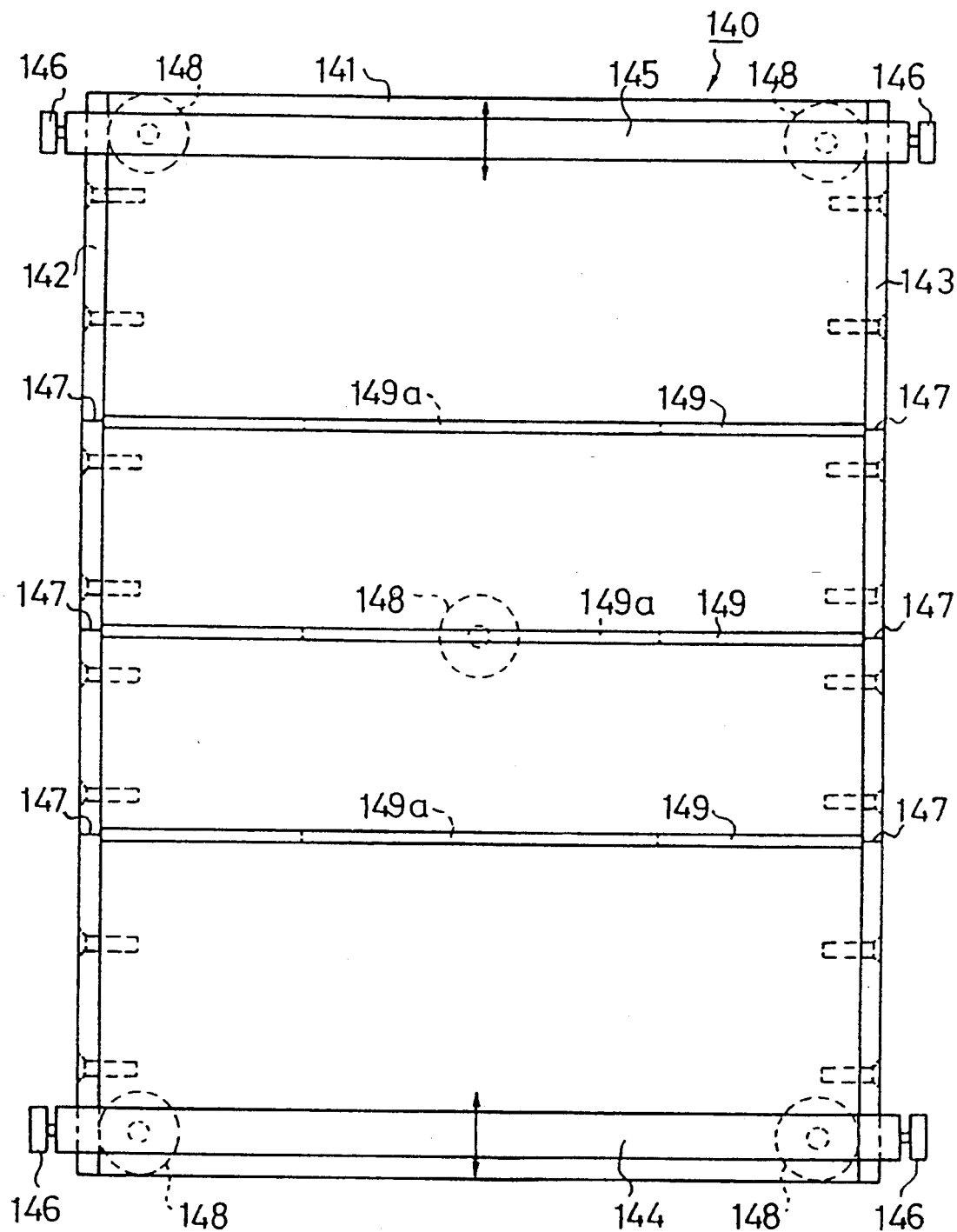

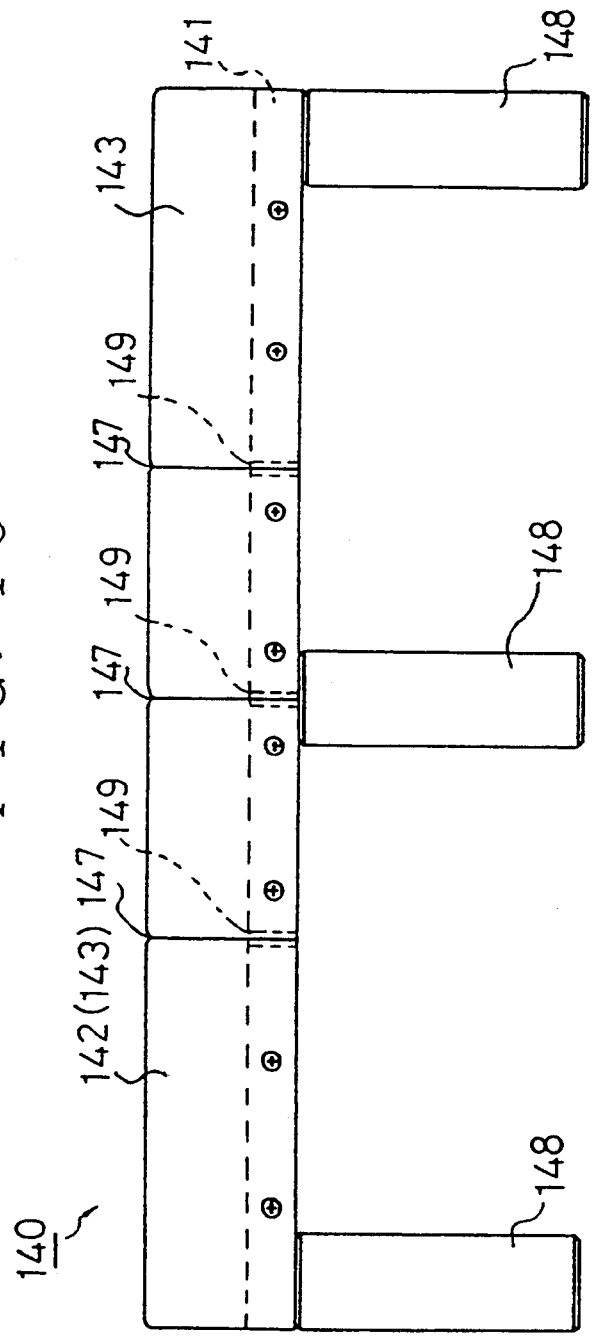

ELECTROPHORETIC MEDIUM FOR ELECTROPHORETIC SEPARATION, GEL HOLDER FOR HOLDING THE SAME MEDIUM, SLAB TYPE ELECTROPHORETIC APPARATUS USING THE SAME MEDIUM AND GEL HOLDER, AND ELECTROPHORETIC GEL CUTTER

FIELD OF THE INVENTION

This invention relates to electrophoretic media for electrophoretic separation, gel holders for holding these media, slab type electrophoretic apparatuses using these media and gel holders and electrophoretic gel cutters.

BACKGROUND OF THE INVENTION

As is well known in the art, the slab type electrophoretic process (i.e., electrophoretic process for causing electrophoresis of a gel in the form of a vertical column) is superior in the operation control property, resolution, etc. to the disk type electrophoretic process, and is particularly superior in the separation of proteins, enzymes and peptites in large quantities. Further, it is sometimes suited for the separation of nucleic acid and physiologically active materials difficultly capable of heat treatment. Thus, it can find extensive applications in various researches and investigations in the biochemical fields. At present, it is generally used for the purity inspection of purified samples of proteins and nucleic acids and also as a most standard test method for the analysis of mixtures.

Thus, extensive researches and investigations have been conducted on electrophoretic media for analysis purposes in order to improve the separation performance or improve the gel strength to make gel more difficult to crumble.

As an example, Japanese Patent Disclosure No. 59543/89 discloses adding water-soluble polymers and denaturing materials to gels obtained through crosslinking polymerization of acrylamide type compounds to improve the brittleness and separability of the gels.

In case where proteins having catalytic activity such as enzymes is purified, a process in which the efficiency of recovery of the specific activity is high, i.e., the efficiency of recovery of intended enzymic protein is high, is more effective, and this is the most important consideration.

However, no research or investigation has been conducted on electrophoretic media with the purpose of separation.

As an example of the application of the principles underlying the electrophoresis to the separation and purification of particular materials, there is a gel holder disclosed in Japanese Patent Laid-Open No. 143651/92 (laid open on May 18, 1992).

Such gel holder used for the separation and purification of particular materials, is large in size because its purpose is the separation of proteins, enzymes, nucleic acids, etc. In addition, the amount of the electrophoretic medium used in one cycle for this end is 5 to 20 times the amount in the case of the usual electrophoresis. Therefore, it is sometimes required to have a strong performance of fulfilling the role of commonly termed "shieving", i.e., separating a sample according to the molecular size.

In another aspect, in a well-known process of recovering the enzymic protein after the electrophoresis, the electrophoretic medium in the intended enzyme part is cut out, and the cut-out medium is subjected to electric extraction by further electrolysis (Ziola. B.R. & Scraba. D.G. 1976, Anal. Biochem., 72, p-p 366-371). In another well-known process, the electrophoretic medium is physically crushed and suspended in a buffer solution for separation of the intended substance by centrifugal separation or filtering (Toshihisa Oshima & Hiroki Sakamoto, Biochem., 60. 5. p-p 374-377, 1988).

In the process using a gel holder for the electric extraction, the electrophoretic medium is cut in large quantities, thus dictating large size apparatus and long process time. In addition, it is liable that the enzyme or protein looses its activity. Therefore, this process is unsuitable. The physically crushing process requires no substantial time until completion of the crushing and recovery. However, it is thought that electrophoretic media are less peculiarly adsorptive with respect to enzymes, and there is a problem that the recovery of enzymic protein is greatly influenced by whether or not the crushing is made satisfactorily.

Therefore, the electrophoretic medium used for the gel holder is required to have the opposed properties that it has sufficient mechanical strength as material for separation at the time of the electrophoresis while being brittle and readily crumbled by physical crushing power at the time of the recovery of the enzymic protein. At present, there is no electrophoretic medium, which can sufficiently meet these two opposed requirements.

With a gel holder proposed by the applicant in an earlier application, the gel accommodated for separation in a gel accommodation section is engaged with projections formed therein. This structure thus is capable of preventing the falling of the gel to a certain extent, and it has been confirmed that purification can be obtained while maintaining the shape of the gel accommodated in the gel accommodation section to a certain extent even where the distance between gel clamping plates exceeds 1 cm, which has been a limit with the prior art mechanisms.

The applicant has conducted further researches and investigations with the earlier proposed gel holder noted above as a basis to reach a conclusion that for reliably preventing the gravitational fall of the gel and thus permitting the slab type electrophoretic analysis with higher accuracy, it is necessary to produce gel, which has a quite novel composition, as well as providing a gel holder suitable for such novel gel and a novel slab type electrophoretic apparatus using such novel gel and gel holder. Further, it is concluded that it is necessary to provide a gel cutter, which can readily cut large size gels extracted for the purpose of large quantity separation.

SUMMARY OF THE INVENTION

The present invention is predicated on the above finding, and its object is to provide collectively all the elements necessary for the slab type electrophoretic analysis for the purpose of large quantity separation, i.e., a novel electrophoretic medium for separation, which permits large quantity electrophoretic gel without possibility of fall-out of the gel from gel holder even if the spacer size thereof is 1 cm, the limit of the prior art mechanisms, an improved gel holder, which can reliably prevent the fall of the medium, a slab type electrophoretic apparatus, which permits highly accurate electrophoretic analysis by using that medium and gel holder, and a gel cutter, which can accurately and safely cut soft, readily deformable and large size gels polyacrylic acid amide or like gels.

Other objects and features of this invention will become understood from the following description with reference to the accompanying drawings.

BRIEF DESCRIPTION OF THE DRAWINGS

FIG. 1 is a graph showing the stress generated when a load is applied to an electrophoretic medium for separation according to the invention, the stress being plotted against time;

FIG. 8 is a plan view showing the electrophoretic gel cutter;

FIG. 10 is a side view showing the same cutter.

DESCRIPTION OF THE INVENTION

Figure 2:
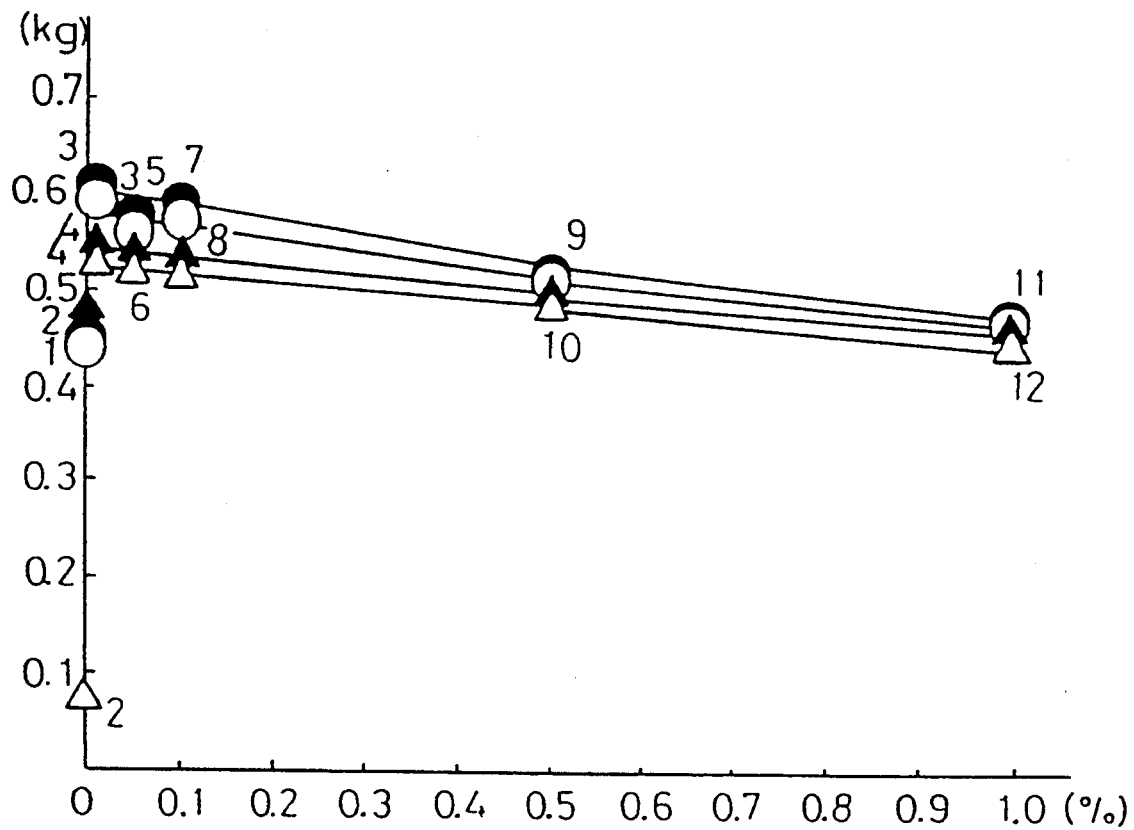
FIG. 2 is a graph showing the "hardness" and "brittleness" of gel in the electrophoretic medium for separation according to the invention, plotted against the amount of water-soluble polymer added to the gel.

To attain the object noted above, the electrophoretic medium for separation according to the invention is obtained by cross-linking polymerizing an acrylic acid amide type compound and contains a water-soluble polymer.

The electrophoretic gel according to the invention is suitable for electrophoretic gels for separation, which have gel thicknesses of 5 mm or above, preferably 20 mm or above.

According to the invention, the acrylic acid amide type compound is either acrylic acid amide or N-methylol acrylamide, and the water-soluble polymer comprises polyethylene glycol, the amount of which is suitably 0.01 to 1% by weight divided by volume with respect to the polymer.

As the water-soluble polymer may be used carboxymethyl cellulose, polyacrylamide, polyethylene glycol, polyglycerol fatty acid ester, polyoxyethylene alkylether, polypropyrene glycol, polyvinyl alcohol, polyvinyl pyrrolidone, etc. but these examples are not limitative.

It is preferable to add a single water soluble polymer, but it is of course possible to add a plurality of different water-soluble polymers in suitable proportions.

The amount of the water-soluble polymer added is suitably 0.01 to 1% by weight divided by volume, preferably 0.01 to 0.5% by weight divided by volume, with respect to the gel solution. If the amount is above 1% by weight divided by volume, the gel is liable to fall off the gel holder to disable the electrophoresis.

The water-soluble polymer or polymers may be added to the gel solution at any time and in any order before the radical polymerization. The addition temperature may be normal temperature, and the addition pH may be in the pH range of the usual buffer solution for the electrophoresis.

The gel holder for holding the electrophoretic gel having the above composition, featured by the invention, comprises a gel accommodation space defined between gel clamping plates and a stopper detachably disposed in a lower portion of the gel accommodation space, the stopper having a plurality of small holes or slits spaced apart.

The slab type electrophoretic apparatus for electrophoresis of the electrophoretic medium having the above composition held by the gel holder having the above construction, featured by the invention, comprises end point detection means for optically detecting the end point of an electrophoresis marker, means for stopping the supply of current to gel electrophoresis means according to information from the end point detection means, and means for detecting the temperature of the buffer solution, in which the gel holder is dipped, and automatically recording detected temperature changes.

The gel cutter for cutting gel obtained after the electrophoresis without causing damage to the gel, featured by the invention, comprises a gel table, on which electrophoretic gel is placed, paired guides provided on the gel table, paired stopper members slidable along and in the longitudinal direction of the guides, securement members provided on the stoppers, and a cutting tool guide grooves formed in the guides, the stopper members being adapted to be held secured in predetermined cutting positions such that they clamp electrophoretic gel placed on the gel table.

EXPERIMENT EXAMPLE 1

This example concerns the constitution of the electrophoretic medium.

Various gel media were prepared, and their physical properties were measured as shown hereinunder.

Methods of preparation of reagents necessary for the gel medium preparation are shown in Table 1 in the separate sheet.

Study was then made on gels obtained through radical polymerization of acrylic acid amide and N-methylol acrylic acid amide.

As the water-soluble polymer polyethylene glycol was used. It was added in 0, 0.01, 0.05, 0.1, 0.5 and 1% by weight divided by volume with respect to the gel solution.

Figure 3:
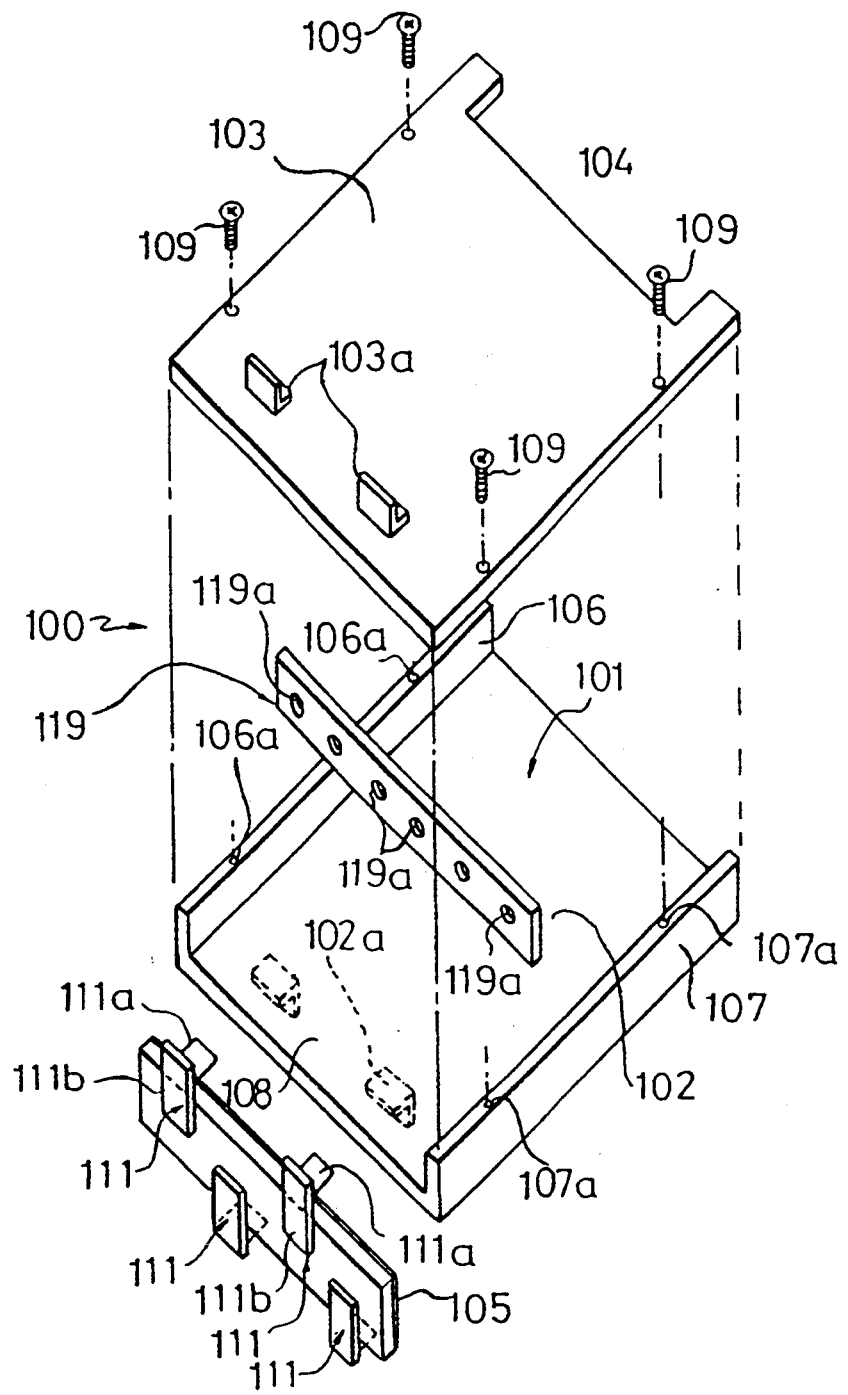
FIG. 3 is an exploded perspective view showing a gel holder suited for the electrophoretic medium for separation.

Into a pressure-bearing glass bottle with a volume of 200 ml, 7.5 ml of solution A and 7.5 ml of solution C or C' shown in Table 2, 14.0 ml of water and polyethylene glycol in amounts shown in FIG. 3 were poured and mixed. The deterioration was carried out by stirring for about 10 minutes. Subsequently, 1.0 ml of solution E as polymerization initiator and 0.015 ml of N,N,N',N'-tetramethyl ethylenediamine (hereinafter abbreviated as TEMED) were added, and the resultant system was gently stirred. The gel solution obtained in this way was poured into a container with a height of 1.2 cm and a diameter of 5.2 cm such as to fully fill the container. At this time, care is taken lest air bubbles should be introduced into the gel solution.

Subsequently, the gel was covered with a film and isolated from air, and in this state the polymerization was initiated. After the polymerization, a gel with a height of 1.2 cm was obtained.

The gel was then taken out from the container and cut into the form of a dice with dimensions of 1.5 cm×1.5 cm using a gel cutter. The cut pieces of gel were used as a sample for the measurement of the mechanical strength.

For the measurement of the mechanical strength, "Leorometer Max RX-1600" manufactured by I.techno Co. was used.

The measurement was carried out under the following conditions.

Temperature of the room: 25.0° C.
Speed (fixed speed) of motion: 100.0 nun/min.
Clearance: 6.0 mm
Height of sample: 12 mm
Plunger diameter: 30.0 mm
Number of rotations in motion: 1
Load range: 1.0 kg FIG. 1 shows stress plotted against time generated by applying the load to the sample while causing vertical reciprocation of the plunger at a constant speed.

Indicated by H in the Figure is the "hardness", which is the maximum value of the stress obtained when force is applied for the first time with the plunger. The stress is expressed in kg.

Indicated by F is the "brittleness", which is a power level sufficient to destroy the substance. The brittleness is again expressed in kg.

When the outermost portion of the sample is destroyed by the plunger at a destruction speed equal to or higher than the plunger speed, a recessed portion is formed in the stress curve as shown in FIG. 1. When the plunger is further lowered to strike the destroyed surface, the stress curve as shown is obtained.

FIG. 2 shows the "hardness" or "brittleness" with the water-soluble polymer amounts added to gel.

It will be seen from the measurement results that the gels obtained by adding water-soluble polymer to acrylic acid amide derivative are superior in the mechanical strength and fragile compared to those incorporating no water-soluble polymer.

EXPERIMENT EXAMPLE 2

An example of electrophoresis for protein separation for the purpose of sample separation will be described.

The reagents necessary for the electrophoresis were prepared in the manners as shown in Table 1. Reference was had to the Davis process.

As the electrophoretic apparatus for separation, the above apparatus was used.

First, two different separation gels having the compositions shown in Table 4 in the separate sheet were prepared.

In a pressure-bearing glass bottle, solution A, solution C, water, and water-soluble polymer were mixed. Deaeration was carried out by stirring for about 30 minutes. Then, solution E and TEMED were added, and the system was stirred slowly.

The gel solution thus obtained was poured into a gel holder comprising acrylic acid plates with a thickness of 2 cm and a width of 19 cm such that the height of the poured gel solution was 12 cm. At this time, care was taken lest air bubbles should be introduced into the gel solution.

Then, water was deposited quietly on the gel surface. By this operation, the operation of gel polymerization was completed within 20 minutes.

After the completion of the polymerization of the separation gels, condensed gels were prepared. Reagents were used as shown in Table 5.

First, 5.0 ml of solution B, 10.0 ml of solution D and 24.0 ml of water were mixed in a pressure-bearing glass bottle. Deaeration was carried out by stirring for about 20 minutes.

Subsequently, 0.04 g of polyethylene glycol, 1.0 ml of solution E and 0.07 ml of TEMED were added, and the resultant system was stirred slowly.

Then, water deposited on the separation gel was removed, then the condensed gel solution was deposited on the separation gel. Then, as in the case of the preparation of the separation gel, water was deposited quietly on the gel surface. By this operation, the polymerization of the gel was completed within 10 minutes.

Now, a case of use of commercially available phosphoglucomutase (E.C.5.4.2.2, purified enzyme, derived from rabbit's muscle, manufactured by SIGMA Co., Ltd.) for separation will be described.

A sample solution was prepared by adding 12 ml of a solution containing 60% by weight divided by volume of glycerol and several drops of solution G shown in Table to 30 ml of an aqueous sample protein solution (containing about 6 mg of protein, and then adding solution B shown in Table B to obtain a total quantity of 50 ml (the sample solution thus prepared being hereinafter referred to as prepared sample).

A lower trough of an electrophoretic trough was preliminarily filled with about 600 ml of solution F (see Table 1). Then, an electrophoretic plate (i.e., a gel holder) after completion of gelation was mounted in the electrophoretic trough. At this time, care was taken lest air bubbles should be introduced into under the gel.

Then, after securing the electrophoretic plate to the electrophoretic trough, an upper trough thereof is filled with solution F. At this time, it was confirmed that there is no leak from the upper trough.

Subsequently, the prepared seunple was poured onto the condensed gel, and then energization was started by setting a constant current of 50 mA. If the sample is an enzyme or like active substance, for preventing temperature rise the electrophoresis is carried out in a low temperature chamber by reducing the current.

After completion of the electrophoresis, the electrophoretic plate is taken out from the electrophoretic trough, and the contained gel was taken out therefrom.

Then, for determining the position of phosphoglucomutase as the intended substance after the electrophoresis, the gel thereafter was cut out in a direction parallel to the electrophoretic direction.

The cut gel portion obtained in this way was actively dyed using a reagent described below, thus confirming the position of the intended enzyme.

Reagent A, which comprises a mixture of 5.0 ml of 0.2 M Tris-HCl with a pH of 8.0, 5.0 ml of 0.1 M MgCl2, 25.0 ml of distilled water, and 0.6 g of agar, was heated to dissolve agar.

Then, the above reagent A was cooled down to 60° C. Then, the total quantity of reagent B shown below was added and mixed.

The reagent B was prepared from 5.0 mg of glucose-1-phosphate and glucose-1,6-diphosphate, 1.0 mg of glucose-6-phosphate dehydrogenase (freeze dry), 0.5 mg of NADP, 0.5 ml of PMS (phenazine methosulfate) solution (1.25 g/ml) and 1.0 ml of MTT (dimethylthiazol tetrazolium) solution (1.0 g/ml).

By depositing the reagent thus obtained by adding the reagent B on the gel after the electrophoresis, the intended enzyme appears as a violet band.

The position of the intended enzyme after the electrophoresis was determined from the mobility of the enzyme, and the corresponding portion of the gel was cut in the perpendicular direction to the electrophoretic direction.

The cut-out gel was finely crushed using a wooden pestle, and then 0.1 M Tris-HCl (with a pH of 7.4) was added. Then, the gel dispersoid was slowly stirred to extract the enzyme into the buffer solution.

Subsequently, the gel and enzyme extraction liquid were separated.

The recovery factor of phosphoglucomutase obtained in this way was measured with respect to the protein amount and activity. The results are shown in Table 5 in the separate sheet.

The protein was measured in a method having reference to Bardford, M., Anal. Biochem., 72, 248, 1976, and the activity was measured in a method having reference to Hideo Chiba, Proteins, Nucleic Acids and Enzymes, 22, 1530-1536, 1977.

As is obvious from the results shown in Table 5, by using the electrophoretic gels incorporating water-soluble polymer for the separation of protein, the protein recovery factor and activity recovery factor could be improved.

Table 5 also shows the results of a phosphoglucomutase recovery test conducted as a comparative test by causing disk electrophoresis between glass disks having an inner diameter of 5 mm and a length of 80 mm, which were used for separation.

As is seen from Table 5, this means, when used for the purification of enzyme, permits recovery of 220 to 240 times the activity in a single electrophoretic cycle, and thus is best suited for the separation of enzymes.

Figure 4:
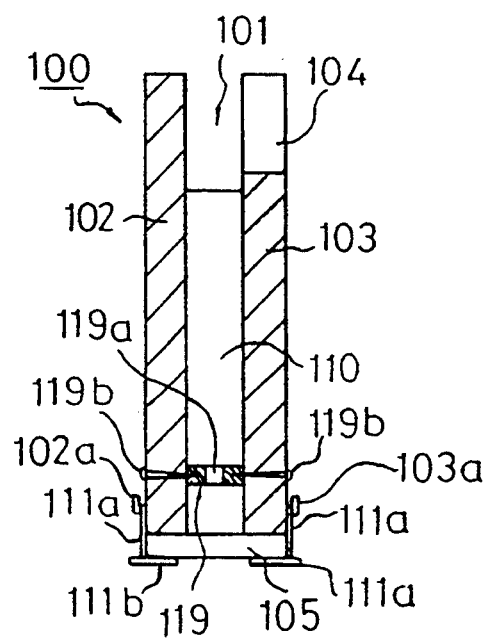
FIG. 4 is a sectional view showing the gel holder.

For the separation of the gels having the compositions noted above, it is suitable to use a gel holder 100 shown in FIGS. 3 and 4.

The gel holder 100, which was used in the above example, comprises a transparent acrylic acid resin plate 102 with each side having a dimension of about 19 cm and a thickness of about 1.0 cm, a transparent acrylic acid resin plate 103 having substantially the same dimension as the plate 102 and having a channel-shaped notched top 104. The acrylic acid resin plate 102 has opposite side walls 106 and 107 such that a space having a width of about 2.0 cm is formed between the acrylic acid resin plates 102 and 103. The lower end 108 of the gel accommodation space 101 formed between the plates 102 and 103, can be sealed by an acrylic acid resin bottom member 105 with the sides thereof provided with packings and capable of being mounted and demounted.

The bottom member 105, as shown in FIGS. 3 and 4, has each of the upper and lower surfaces provided with two mounting members 111, which are well-known corner catch clips or the like. The mounting members 111 are adapted such that they are locked in their hooked state by hooking their rings 111a in slotted hooks 102a and 103a formed in the acrylic acid resin plates 102 and 103 and then turning operating members 111b coupled to the rings 111a. The slotted hooks 102a and 103a are provided with ceramic coating, or they are provided at positions not dipped in lower electrophoretic buffer solution 128 to be described later.

Above the bottom member 105, a stopper 119 having a plurality of small holes 119a is detachably mounted by screws 119b on the plates 102 and 103. The screws 119b as the means for securing the stopper 119b are by no means limitative; for example, it is possible to form opposed surfaces of the plates 102 and 103 with slits arranged at a predetermined interval and insert the stopper 119 in such slits for securing the same.

The stopper 119 is made of such material as acrylic acid resin, Telfon and Juracon. To cause current through gel, it has to be spaced apart with respect to the bottom member 105, and thus its area is desirably 10 to 95% of the area of the opening which is closed by the bottom member 105. It can not be made of a metal capable of electrolytic decomposition.

Figure 5:
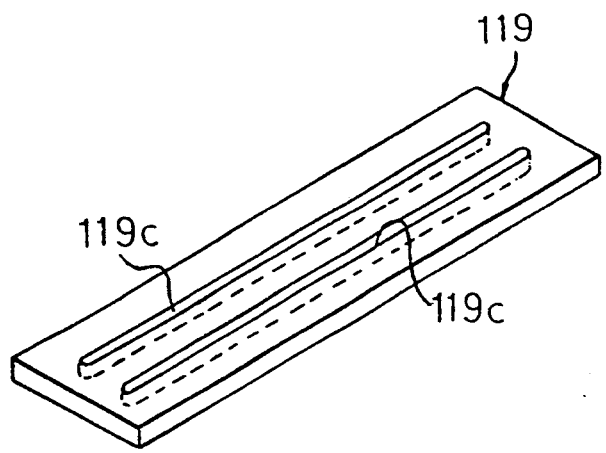
FIG. 5 is a perspective view showing a different example of a stopper in the same gel holder.

While six small openings 119a are shown, this number is by no means limitative, and it is possible to form a suitable number of holes. Also, the holes may not be circular in shape; for instance, it is possible to form a plurality of slits 119c as shown in FIG. 5. As a further alternative, it is possible to form notches at the opposite ends of the stopper 119.

The stopper 119 having the above construction is desirably set at a position mid way in the height of the gel holder 100.

While in the above example, the gel accommodation space 101 was shown to be set to 2.0 cm or above, according to the invention sufficient effects could be obtained by setting the gel accommodation space 101 to 5 mm or above.

Figure 6:
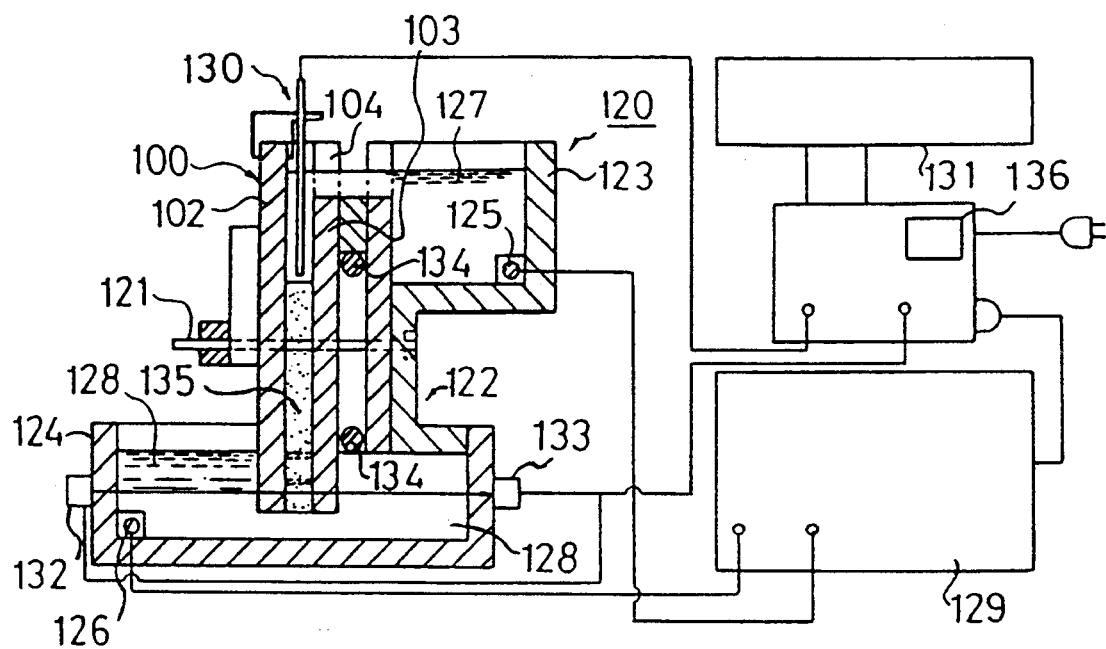
FIG. 6 is a schematic side view, partly in section, showing a slab type electrophoretic apparatus suitable for use with the same electrophoretic medium for separation and gel holder.
Figure 7:
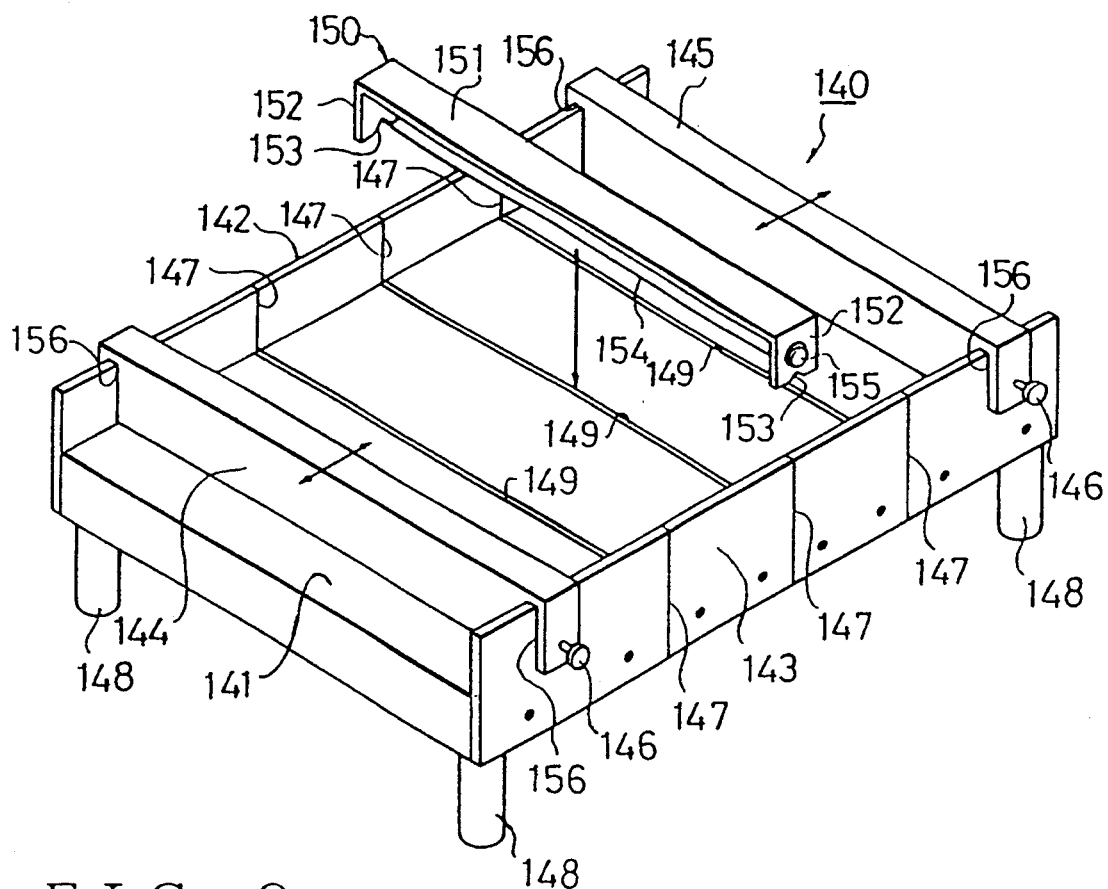
FIG. 7 is an exploded perspective view showing an electrophoretic gel cutter.

For carrying out electrophoresis by accommodating the gel having the composition noted above in the gel holder 100 having the above construction, a slab type electrophoretic apparatus 120 shown in FIG. 6 is suitable.

The slab type electrophoretic apparatus 120 comprises a stopper 121 for securing and supporting the gel holder 100, an electrophoretic trough 122, an upper buffer solution trough 123 formed above the electrophoretic trough 122, a lower buffer solution trough 124 formed below the electrophoretic trough 122, an anode electrode 125 disposed in the upper buffer solution trough 123, a cathode electrode 126 disposed in the lower buffer solution trough 124, upper electrophoretic buffer solution 127 accommodated in the upper buffer solution trough 123, lower electrophoretic buffer solution 128 accommodated in the lower buffer solution trough 124, a power source 129 for electrophoresis, a temperature sensor 130 disposed in the upper buffer solution trough 123, a recorder 131 for recording temperature changes detected by the temperature sensor 130, a light source 132 disposed in the lower buffer solution trough 124, a color sensor 133 for receiving light emitted from the light source 132, and a switch (not shown) for stopping current supply by detecting a change specific in or a specific wavelength of a photoelectric voltage conversion received by the color sensor 133. Reference numeral 110 designates the electrophoretic gel having the above composition, 134 a seal packing, and 130 a controller for current supply/stop control and temperature control. According to the invention, the light source 132 need not be disposed in a chamber, in which ordinary illumination can be ensured. However, for stable detection it is desirably provided in a dark room or a place subject to illumination changes.

The temperature sensor 130 is made of a material free from electrolytic decomposition even when dipped in the buffer solution for electrophoresis; for example, it is desirable to cover a temperature sensor section with glass or the like.

The temperature detected by the temperature sensor 130 is automatically recorded by the recorder 131 as numerical values or as a graph. The recorder 131 has a construction like that of the well-known recorder, and therefore it is not described in detail.

The light source 132 and color sensor 133 are mounted on opposed walls of the lower buffer solution trough 124, which is formed by a transparent material at positions such that light is not blocked between them.

As the color sensor 133 may be used a well-known light-receiving element corresponding to the material of an electrophoretic marker.

The controller 136 is a well-known microprocessor unit(MPU). It recognizes a change in or a specific wavelength of photoelectric conversion voltage of the color sensor 133 and stops the supply of current from the electrophoretic power source 129 upon detection of the reaching of a predetermined voltage or wavelength by the measured value. Alternatively, the controller 136 may be constructed such that it can automatically cause heat generation in heating means (not shown) according to temperature information from the temperature sensor 130 so as to maintain electrophoresis at a predetermined temperature. Specifically, a low temperature of 0° to 4° C. is set for the electrophoresis to prevent loss of activity of the enzyme.

As for the other structure other than described above, the details of the mechanism and operation are the same as those of the corresponding components of the well-known slab type electrophoresis apparatus, so they are not described here.

Now, a case of separating and purifying dehydrogenase by using the gel holder having the above construction will be described. In the first place, the gel holder 100 is set in the gel production table.

Then, electrophoretic gel 110 having the composition noted before is deaerated using an aspirator and then poured into the gel accommodation space 101 by taking care lest air bubbles should be generated. The height of the poured gel is about 13 cm. Then, water is deposited quietly (to a height of about 2 mm), and then the system is dipped in hot water at 30° C. for 60 minutes for gelation.

Thereafter, water is removed, and the condensed gel solution was charged onto the electrophoretic gel 110 and perfectly gelated. Then, the bottom member 105 is removed by loosening the mounting members 111 in a lower part of the gel holder 100. Then, the gel holder is taken out and mounted in the electrophorettic trough 122 along with the stopper 121, as shown in FIG. 6.

Now, the upper and lower buffer solutions 123 and 124 are filled with the electrophoretic buffer solutions 127 and 128. Meanwhile, to the enzyme sample liquid are added adequate quantities of about 10% glycerin and buffer solution for the condensed gel and several drops of BPB as electrophoretic marker. Of course, when carrying out electrophoresis in the acidic range according to the invention, as the electrophoretic marker may suitably be used a well-known marker such as Methyl Green. In the case of the electrophoresis in the acidic region, the anode and cathode electrodes 125 and 126 are reversed.

The sample solution prepared in this way is deposited quietly on the gel for condensation using a pippet or a pulsation-free pump. The maximum amount of sample to be provided at a time is 30 to 120 ml, and the corresponding height of the sample solution bath is about 3 cm. When the amount of the sample is large, it is possible to cause electrophoresis for a predetermined period of time and, when the sample is rendered to be a condensed gel to a certain extent, 20 to 50 ml of the sample solution if added for continual electrophoresis.

Until the marker BPB becomes the separation gel, the electrophoresis is done for several hours with a current of about 50 mA and then with a current of 60 to 100 mA.

When the marker BPB reaches a position of 30 mm from the lower end of the electrophoretic gel 110 after the electrophoresis, the wavelength of the light output of the light source 132 is changed by the marker BPB, and the changed light is received by the color sensor 133. The voltage change at this time is about 500 mV, and the controller 136 can reliably discriminate this change and automatically stop the supply of current from the electrophoretic power source 129 to the anode and cathode electrodes 125 and 126. Thus, the electrophoresis can be stopped automatically in the optimum state of electrophoresis. Of course, it is possible to construct the means for stopping the current supply from the electrophoretic power source 129 such that it does not discriminate the quantitative change in the photoelectric conversion voltage but it stops the current supply according to the wavelength balance, for instance, which is changed with the marker BPB. With this structure, it is possible to obtain the same effects. It is further possible to cause flickering of a lamp or driving of a buzzer when the current supply is automatically stopped.

With the slab type electrophoretic apparatus 120 described above, it is possible to permit instantaneous measurement of the electrophoretic temperature by the temperature sensor 130 and automatic heat generation control of the heating means (not shown) according to the temperature information obtained by the temperature sensor 130.

Subsequently, the gel holder 100 is taken out quickly from the slab type electrophoretic apparatus 120 as the embodiment of the invention, then one of the electrophoretic plates, i.e., the acrylic acid resin plate 103, is taken out, and then an end portion of the electrophoretic gel 110 is cut out to a width of about 5 mm.

The cut portion of gel is then dipped in 50 ml of a reaction solution, which is contained in a glass tray and contains 0.1 M of Tris-HCl buffer solution (with a pH of 8.0), 0.3 mM of NAD (nicotinamide adenin dinucleotide), 0.8 mM of base material, 0.2 mM of phenazine methosulfate and 0.8 mM of MTT (dimethylthiazol tetrazolium) for active dying at 37° to 50° C. for several minutes. When red-violet activity band appears, the gel piece is taken out and returned to the initial position. Then a gel portion at the position of the activity band is cut out horizontally to a width slightly greater than the band width. This gel portion is actively dyed in the same manner as above, and its other portions than the portion, in a straight activity band appears, are removed.

Then, the actively dyed gel is sliced into rectangular pieces about 5 mm in width and then crushed together with a buffer solution (with a pH of 7.2) by using a Poter type Teflon homogenizer (fairly loose fitted glass-Teflon homogenizer)(with a volume of 50 ml) while ice cooling the system. The gel solution thus obtained by crushing is subjected to centrifugal separation (20,000 xg, 10 minutes, 4° C.) to obtain upper enzyme extraction solution. Also, to the settled gel is added a small amount of buffer solution to produce a suspension for repeated centrifugal separation thereof, thus obtaining a second enzyme extraction solution. The method of preparation described above is applicable to the purification not only of the dehydrated enzymes but also to many other enzymes capable of active dying such as NAD and NADP. Further, the method may be applied to purification without active dying but by obtaining the Rf value likewise. Particularly, it is satisfactory separation means for the purification of highly thermally stable enzymes such as heat-liking bacteria enzymes.

For cutting the above electrophoretic gel to the desired size and shape, a gel cutter as shown in FIGS. 7 to 10 is used desirably.

It is very difficult to cut an electrophoretic gel having as large size as 5 mm or above, particularly a soft and readily deformable gel such as a polyacrylamide gel, accurately and safely to a desired size. With the instant gel cutter it is possible to cut such gel accurately and safety without causing damage thereto.

FIGS. 7 to 10 show the the electrophoretic gel cutter 140. The gel cutter is made of a synthetic resin such as an acrylic acid resin or a Juracon resin. As shown, it comprises a gel table 141 for supporting the electrophoretic gel placed thereon, pair guides 142 and 143 provided on top of the gel table 141 and facing each other, paired stopper members 144 and 145 mounted on the guides 142 and 143 for sliding along the same in the longitudinal direction thereof and facing each other, securement members 146 each mounted on each of the stopper members 144 and 145, wire guide grooves 147 formed in the guides 142 and 143 facing each other, a plurality of legs 148 secured to the underside of the gel table 141, and a cutter 150 for cutting the electrophoretic gel. The gel cutter 140 is desirably milky white in color to permit ready observation of color generation when making activity dying on the gel table 141. However, this is by no means limitative.

As shown in the Figures, the gel table 141 is a flat plate. Its top is formed with three straight grooves 149 extending in a direction perpendicular to the longitudinal direction of the guides 142 and 143 and communicated with the respective three wire guide grooves 147 of the guides 142 and 143.

Figure 9:
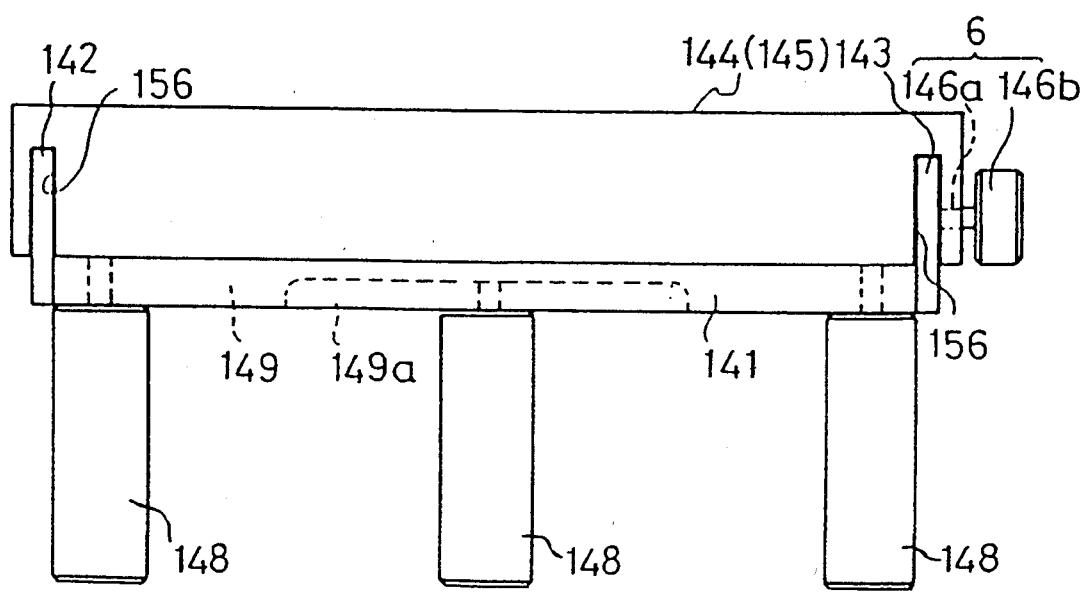
FIG. 9 is an elevational view showing the same cutter.

As is clearly seen from FIG. 9, each groove 149 vertically penetrates the gel table 141, and its central lower portion is formed with an elongate coupling portion 149a to prevent a wire 154 of the cutter 150 to be described later from sagging slightly and becoming unable to cut a central portion of the electrophoretic gel being cut on the gel table 141. Thus, the gel cutter can completely cut the gel.

The number of the grooves 149 is not limited to three. However, with the provision of the three grooves it is possible to cut the electrophoretic gel into three portions, i.e., an upper, an intermediate and a lower portion, without moving the gel along the gel table. The grooves 149 are desirably spaced apart at a uniform interval, for instance 1 to 2 cm. Further, if their width is small, the gel can be cut clearly. For example, it is desirably 0.2 mm or below. The depth of the grooves 149 is desirably about 5 mm when the sagging of the wire 154 at the time of the cutting is taken into considerations. The coupling portion 149a formed on the central lower portion of the groove 149 may not be elongate in shape; for example, it may be triangular or circular in shape.

The paired guides 142 and 143 are made from elongate plates and each have the three vertical wire guide grooves 147 noted above, which are formed at positions corresponding to the positions of the respective three grooves 149 of the gel table 141.

The three wire guide grooves 147 have a width permitting the insertion of the wire 154 of the cutter 150 to be described later. The upper and lower ends of the opposed surfaces of each wire guide groove 147 in the guides 142 and 143, roundedly chamfered so that the wire 154 can be smoothly guided into and out of the groove. The wire guide grooves 147 desirably have a width of 0.125 to 0.2 mm to obtain smoothly cut surface of the electrophoretic gel. However, it is difficult to form such very narrow grooves. Accordingly, it is desirable to form a wire guide groove by holding cut pieces of guide 142 or 143 such as to form a clearance of 0.2 mm or below between them.

The paired guides 142 and 143 also function as guide rails for the paired stopper members 144 and 145.

The paired stopper members 144 and 145 are each made from a flat plate having a predetermined width. Each of them has engagement grooves 156 formed adjacent the opposite ends for being engaged on the guides 142 and 143. It also has a threaded hole open at each end, with the securement member 146 noted above being fitted in the threaded hole. Of course, the stopper members 144 and 145 have a height size such that their lower end is in contact with the gel table 141 and that the paired engagement grooves 156 are spaced apart by a distance substantially equal to the distance between the opposed walls of the guides 142 and 143.

Each of the securement members 146 has a threaded pin 146a screwed in the threaded hole noted above and a handle portion 146b coupled to the projecting end of the threaded pin 146a. The securement member 146 may be provided on one or each end of the stopper members 144 and 145.

The stopper members 144 and 145 are secured in a predetermined position by sliding them to positions to clamp the electrophoretic gel placed on the gel table 141 and tightening the securement members 146 such that the gel is compressed to a certain extent.

The legs 148 provided on the gel table 141 have a height of 3 to 10 cm to hold the gel table at a predetermined height position such that the electrophoretic gel can be cut by pushing down the wire 154 in one stroke. They are secured by screws to the four corners and the center of the underside of the gel table. Of course, the number and positions of the legs 148 may be suitably selected by taking the mechanical strength into considerations. It is possible to provide the underside of each leg 148 with a rubber packing (not shown) to provide an anti-slip effect. Of the plurality of legs 148 the central leg 148 shown in FIG. 8 is secured such that its upper threaded portion does not project upward from the top of the coupling portion 149a of the groove 149.

The cutter 150 comprises a substantially channel-shaped frame 151 having opposed depending end portions 152 each formed with V-shaped notch 153, a wire 154 stretched taut between these V-shaped notches 153, and a tension adjuster 155 for adjusting the tension in the wire 154. By turning the tension adjuster 155 the stretched state of the wire 154 for cutting the electrophoretic gel can be adjusted to an adequately taut state.

The wire 154 is suitably steel wire, piano wire, fishing yarn, etc. having low elongation and contraction property.

Now, a case of cutting electrophoretic gel with the gel cutter 140 having the above construction will now be described.

After completion of electrophoresis with the slab type electrophoretic apparatus 120, the electrophoretic plates with the electrophoretic gel supported thereby are taken out and placed on a horizontal base. Then, screws coupling the plates are removed, and then 60% concentration glycerol is thinly coated to prevent excessive drying of the gel surface. Further, 60% concentration glycerol is provided with a syringe between the electrophoretic gel and the elelctrophoretic plate.

Then, using a spatula the gel is lifted from the plate and tilted together with the plate to be brought onto the gel table 141, and then it is set at a predetermined cutting position. If the position is known from a preliminary test, the position is calculated on the basis of the Rf value (rate of flow value). When the position of the intended substance is determined, the cutting positions of the gel are set such that they correspond to the grooves 149. Then, the stopper members 144 and 145 are moved along the paired guides, in their state of urging the gel to a certain extent they are secured by tightening. The urged state of the electrophoretic gel at this time is such that the gel does not float up from the gel table 141 and that the surface of the gel does not become wavy.

When the electrophoretic gel has been secured at the cutting position in this way, the wire 54 is lowered along the wide guide grooves by gripping the cutter 150 with the wire 54 directed down. In this way, the gel is cut.

When determining the cutting position by dying, a portion of the gel placed on the gel table 141 may be cut in a direction parallel to the electrophoretic direction.

INDUSTRIAL UTILITY

As has been described in the foregoing, the electrophoretic medium according to the invention is composed of a gel solution and contains a water-soluble polymer. Thus, it is possible to obtain a sufficient mechanical strength of the medium as separation material in the electrophoresis. Also, the medium is very fragile and can be readily crushed by applying a crushing force for recovering enzymic protein. It is thus possible to greatly improve the enzymic protein recovery character, and the medium is thus best suited as separation medium.

Further, with the gel holder according to the invention, by mounting the stopper members it is possible to hold a soft gel or a very slippery gel at a fixed position. It is thus possible to obtain reliable separation and refinement of the intended substance without causing denaturing thereof.

Further, with the slab type electrophoretic apparatus, without setting any measurement condition in advance it is possible to detect the electrophoretic state of the sample automatically and terminate the electrophoresis automatically under the optimum conditions. Further, it is possible to continuously measure the buffer solution temperature, which is very important in view of obtaining electrophoretic conditions for maintaining the enzymic function. Further, it is possible to separate and purify a large quantity of enzymes or like phisiological substances at a time in a very simple operation.

Further, with the electrophoretic gel cutter according to the invention even large size electrophoretic gels can be cut very accurately and safely to desired sizes. Particularly, it is possible to cut soft and readily deformable electrophoretic gels such as polyacrylamide gel in a pressurized state. It is thus possible to cut polyacrylamide gel, which has heretofore been very difficult to cut, accurately and safely and without causing damage.

Although the invention has been described with respect to specific embodiments for a complete and clear disclosure, the appended claims are not to be thus limited but are to be construed as embodying all modifications and alternative constructions that may occur to one skilled in the art which fairly fall within the basic teaching herein set forth.

TABLE 1

Method of reagent preparation for gel production

| Reagent name | Method of preparation | |
|---|---|---|
| A. Buffer solution for separation gel | Tris(hydroxymethyl) aminomethane | 18.1 g |
| | 1N HCl with pH of 8.9 | about 24 ml |
| | Water | 100 ml |
| B. Buffer solution for condensed gel | Tris(hydroxymethyl) aminomethane | 6.0 g |
| | 1N HCl with pH of 6.8 | about 48 ml |
| | Water | 100 ml |
| C. Separation gel solution | N-methylolacrylamide | 29.2 g |
| | N,N'-methylenebis-acrylamide | 0.8 g |
| | water | 100 ml |
| C'. Separation gel solution | Acrylamide | 29.2 g |
| | N,N'-methylenebis-acrylamide | 0.8 g |
| | Water | 100 ml |
| D. Condensed gel solution | N-methylolacrylamide | 10.0 g |
| | N,N'-methylenebis-acrylamide | 2.5 g |
| | Water | 100 ml |
| D'. Condensed gel | Acrylamide | 10.0 g |
| | N,N'-methylenebis-acrylamide | 2.5 g |
| | Water | 100 ml |
| E. Ammonium persulfate solution | Ammonium persulfate | 150 mg |
| | Water | 10 ml |
| F. Electrophoretic electrode buffer solution | Tris(hydroxymethyl) aminomethane | 3.0 g |
| | Glycine | 14.4 g |
| | Water | 1,000 ml |
| G. BPB solution | Bromophenol blue | 10 mg |
| | Glycerol | 1 ml |
| | Water | 10 ml |

TABLE 2

Reagent composition for mechanical strength measurement gel preparation, part 1

| Reagent | Kind of gel Acrylamide | N-methylolacrylamide |
|---|---|---|
| A | 7.5 ml | 7.5 ml |
| C | 0.0 ml | 7.5 ml |
| C' | 7.5 ml | 0.0 ml |
| Water | 14.0 ml | 14.0 ml |
| E | 1.0 ml | 1.0 ml |
| TEMED*2 | 0.015 ml | 0.015 ml |

*2) TEMED: N,N,N',N'-tetramethylethylenediamine

TABLE 3

Reagent composition for mechanical strength measurement gel preparation, part 2 (Amount of polyethylene glycol added when preparing gel according to the composition shown in Table 2)

| Amount of polyethylene glycol | | Gel No. | |
|---|---|---|---|
| % | Amount added (mg) | Acrylamide | N-methylol-acrylamide |
| 0 | 0 | 1 | 2 |
| 0.01 | 3 | 3 | 4 |
| 0.05 | 15 | 5 | 6 |
| 0.1 | 30 | 7 | 8 |
| 0.5 | 150 | 9 | 10 |
| 1 | 300 | 11 | 12 |

TABLE 4

Preparation of polymerization solution of separation gel and condensed gel

| | Gel No. | |
|---|---|---|
| Reagent | 2 | 8 |
| Separation gel | | |
| A | 135.0 ml | 135.0 ml |
| C | 135.0 ml | 135.0 ml |
| Water | 252.0 ml | 252.0 ml |
| Polyethylene glycol | 0.0 g | 0.54 g |
| E | 18.0 ml | 18.0 ml |
| TEMED | 0.27 ml | 0.27 ml |
| Condensed gel | | |
| B | 5.0 ml | 5.0 ml |
| D | 10.0 ml | 10.0 ml |
| Water | 24.0 ml | 24.0 ml |
| Polyethylene glycol | 0.0% | 0.04 g |
| E | 1.0 ml | 1.0 ml |
| TEMED | 0.07 ml | 0.07 ml |

TABLE 5

Results of recovery of phosphoglucomutase after electrophoresis

| | Gel No. | | | |
|---|---|---|---|---|
| | 2 | | 8 | |
| Electrophoretic method | Disk | Inven- | Disk | Inven- |
| Before E.P. protein (mg) | 0.03 | 6 | 0.03 | 6 |
| Before E.P. activity (units) | 1.2 | 240 | 1.2 | 240 |
| After E.P. protein (mg) | 0.005 | 1.0 | 0.009 | 1.99 |
| After E.P. protein recovery factor (%) | 15.8 | 16.7 | 30.0 | 33.2 |
| After E.P. activity (units) | 0.03 | 7.2 | 0.07 | 15.6 |
| After E.P. activity recovery factor (%) | 2.5 | 3.0 | 5.8 | 6.5 |

What is claimed:

1. An electrophoretic medium for separation composed of an electrophoretic gel medium obtained through crosslinking polymerization of an acrylamide compound and containing a water-soluble polymer in an amount of 0.01 to 0.5% weight divided by volume with respect to the gel medium.

2. The electrophoretic medium for separation according to claim 1, wherein said acrylamide compound is acrylamide or N-methyl acrylamide, and wherein said water-soluble polymer is polyethylene glycol.

3. A gel holder comprising a gel accommodation space formed between paired plates for sandwiching an electrophoretic gel there between and a stopper detachably disposed in a lower portion of said gel accommodation space, said stopper having a plurality of small holes or slits.

4. A slab electrophoretic apparatus comprising an end point detection means for optically detecting the end point of an electrophoretic marker, means for stopping the supply of current to gel electrophoresis means according to information from said end point detection means and means for detecting the temperature of a buffer solution in an electrophoretic trough, gel holder being dipped in said buffer solution, and automatically recording detected temperature changes.

5. An electrophoretic gel cutter comprising a gel table for supporting an electrophoretic gel placed thereon, paired guides provided on said gel table, paired stopper members mounted on said guides for sliding therealong in the longitudinal direction, securement members mounted on said stopper members, and cutting member guide grooves formed in said paired guides, said stopper members being capable of being secured at a predetermined cutting position such as to urge the electrophoretic gel placed on said gel table.

6. The electrophoretic gel cutter according to claim 5, wherein the top surface of said gel table is formed with grooves communicating with said cutting member guide grooves formed in said guides.

7. The electrophoretic gel cutter according to claim 5, which further comprises a plurality of legs secured to the underside of said gel table such as to hold said gel table at a predetermined height position.

8. The electrophoretic gel cutter according to claim 5, which further comprises a cutter member including a channel-shaped frame having opposite end plates having V-shaped notches, a wire stretched between said V-shaped notches, and means for adjusting the stretched state of said wire.

9. A method of electrophoresis for separation comprising the steps of
obtaining an electrophoretic medium through crosslinking polymerization of an acrylamide compound containing a watersoluble polymer,
providing a gel holder comprising a gel accommodation space formed between paired plates for sandwiching an electrophoretic gel therebetween and a stopper detachably disposed in a lower portion of said gel accommodation space, said stopper having a plurality of small holes or slits,
accommodating the electrophoretic medium in the gel holder,
providing a slab electrophoretic apparatus having an electrophoretic trough, an end point detection means for optically detecting the end point of an electrophoretic marker, means for stopping the supply of current to gel electrophoresis means according to information from said end point detection means, means for detecting the temperature of a buffer solution in said electrophoretic trough, and means for automatically recording detected temperature changes, and
setting the gel holder in the electrophoretic apparatus, the gel holder being dipped 10. The method according to claim 9, wherein said acrylamide compound is acrylamide or N-methyl acrylamide, and wherein said water-soluble polymer is polyethylene glycol and contained in an amount of 0.01 to 1% by weight divided by volume with respect to the polymer.

11. An electrophoretic apparatus for separation comprising an electrophoretic medium obtained through cross-linking polymerization of an acrylamide compound and containing a water-soluble poisoner, a gel holder comprising a gel accommodation space formed between paired plates for sandwiching said electrophoretic medium therebetween, and a stopper detachably disposed in a lower portion of said gel accommodation space, said stopper having a plurality of small holes or slits, and a slab electrophoretic apparatus having an end point detection means for optically detecting the end point of an electrophoretic marker, means for stopping the supply of current to gel electrophoresis means according to information from said end point detection means, and means for detecting the temperature of a buffer solution in an electrophoretic trough, said gel holder being dipped in said buffer solution, and automatically recording detected temperature changes.

12. The electrophoretic apparatus according to claim 11, wherein said acrylamide compound is acrylamide or N-methyl acrylamide, and wherein said water-soluble polymer is polyethylene glycol and contained in an amount of 0.01 to 1% by weight divided by volume with respect to the polymer.

13. The electrophoretic apparatus for separation according to claim 11, further comprising an electrophoretic gel cutter, said electrophoretic gel cutter comprising a gel table for supporting said electrophoretic medium place thereon, paired guides provided on said gel table, paired stopper men, hers mounted on said guides for sliding therealong in the longitudinal direction, securement members mounted on said stopper members, and cutting member guide grooves formed in said paired guides, said stopper members being capable of being secured at a predetermined cutting position such as to urge the electrophoretic gel placed on said gel table.

14. The electrophoretic apparatus for separation according to claim 13, wherein the top surface of said gel table is foraged with grooves communicating with said cutting member guide grooves formed in said guides.

15. The electrophoretic apparatus for separation according to claim 13, wherein said electrophoretic gel cutter further comprises a plurality of legs secured to the underside of said gel table such as to hold said gel table at a predetermined height position.

16. The electrophoretic apparatus for separation according to claim 13, wherein said electrophoretic gel cutter further comprises a cutter member including a channel-shaped frame having opposite end plates having V-shaped notches, a wire stretched between said V-shaped notches, and means for adjusting the stretched state of said wire.

17. The electrophoretic apparatus for separation according to claim 14, wherein said electrophoretic gel cutter further comprises a cutter member including a channel-shaped frame having opposite end plates having V-shaped notches, a wire stretched between said V-shaped notches, and means for adjusting the stretched state of said wire.

18. An electrophoretic method for separation comprising obtaining an electrophoretic medium through cross-linking polymerization of an acrylamide compound containing a water-soluble poisoner, providing a gel holder having a gel accommodation space formed between paired plates for sandwiching an electrophoretic medium therebetween, and a stopper detachably disposed in a lower portion of said gel accommodation space, said stopper having a plurality of small holes or slits, accommodating said electrophoretic medium in the gel holder, providing a slab electrophoretic apparatus comprising an end point detection means for optically detecting the end point of an electrophoretic marker, means for stopping the supply of current to gel electrophoresis means according to information from said end point detection means and means for detecting the temperature of a buffer solution in an electrophoretic trough, setting the gel holder in the electrophoretic apparatus, said gel holder being dipped in said buffer solution, automatically recording detected temperature changes, providing an electrophoretic gel cutter comprising a gel table for supporting an electrophoretic gel placed thereon, paired guides provided on said gel table, paired stopper members mounted on said guides for sliding therealong in the longitudinal direction, securement members mounted on said stopper members, and cutting member guide grooves formed in said paired guides, said stopper members being capable of being secured at a predetermined cutting position such as to urge the electrophoretic medium placed on said gel table, and cutting the electrophoretic medium with the electrophoretic gel cutter.

19. The electrophoretic method according to claim 18, wherein the top surface of said gel table is formed with grooves communicating with said cutting member guide grooves formed in said guides.

20. The electrophoretic method according to claim 18, wherein said gel cutter further comprises a plurality of legs secured to the underside of said gel table such as to hold said gel table at a predetermined height position.

21. The electrophoretic method according to claim 18, wherein said gel cutter further comprises a cutter member including a channel-shaped frame having opposite end plates having V-shaped notches, a wire stretched between said V-shaped notches, and means for adjusting the stretched state of said wire.

22. The electrophoretic method according to claim 18, wherein said acrylamide compound of said electrophoretic medium is acrylamide of N-methyl acrylamide, and wherein said water-soluble polymer is polyethylene glycol and contained in an amount of 0.01 to 1% by weight divided by volume with respect to the polymer.

* * * * *